United States Patent
Hallquist

(10) Patent No.: US 7,945,432 B2
(45) Date of Patent: May 17, 2011

(54) SPOT WELD FAILURE DETERMINATION METHOD IN A FINITE ELEMENT ANALYSIS

(75) Inventor: John O. Hallquist, Livermore, CA (US)

(73) Assignee: Livermore Software Technology Corporation, Livermore, CA (US)

( * ) Notice: Subject to any disclaimer, the term of this patent is extended or adjusted under 35 U.S.C. 154(b) by 433 days.

(21) Appl. No.: 12/324,595

(22) Filed: Nov. 26, 2008

(65) Prior Publication Data

US 2010/0131256 A1 May 27, 2010

(51) Int. Cl.
 G06G 7/48 (2006.01)
 B23K 9/28 (2006.01)
 A47J 36/02 (2006.01)
 G01N 3/20 (2006.01)

(52) U.S. Cl. .................. 703/8; 703/6; 703/7; 219/86.1; 228/101; 73/851

(58) Field of Classification Search .................. 703/6–8; 219/86.1; 228/101; 73/851
See application file for complete search history.

(56) References Cited

U.S. PATENT DOCUMENTS

| | | | |
|---|---|---|---|
| 2,004,619 A * | 6/1935 | Tarbox | 219/115 |
| 7,038,700 B2 * | 5/2006 | Kawaguchi et al. | 345/646 |
| 7,640,146 B2 * | 12/2009 | Nutwell et al. | 703/2 |
| 7,672,819 B2 * | 3/2010 | Kumagai | 703/6 |
| 7,752,917 B2 * | 7/2010 | Tomioka | 73/841 |
| 2003/0058259 A1 * | 3/2003 | Kawaguchi et al. | 345/646 |
| 2003/0229476 A1 | 12/2003 | Naganarayana et al. | |
| 2004/0148143 A1 * | 7/2004 | Deobald et al. | 703/2 |

(Continued)

FOREIGN PATENT DOCUMENTS

EP 1742033 A1 1/2007

(Continued)

OTHER PUBLICATIONS

"An investigation on Spot Weld Modeliing for Crash Simulation with LS-DYNA"; F Seeger et al; 4. LS-DYNA Anwenderforum, Bamberg 2005; pp. B-1-1 to B-1-12.*

(Continued)

*Primary Examiner* — Kamini S Shah
*Assistant Examiner* — Akash Saxena
(74) *Attorney, Agent, or Firm* — Roger H. Chu

(57) ABSTRACT

Each spot weld in a structure is represented by a cluster of at least one solid element in a finite element analysis model of the structure. Each spot weld is used for tying together two parts. Each of the two parts are generally represented or modeled as a number of two-dimension shell elements. Since the tie-connection between the spot weld and the two parts can be located arbitrarily within the respective part, the shell elements representing the two parts do not have to be aligned in space. The only requirement is the two shell elements must be overlapped each other such that the spot weld can tie the two shell elements (i.e., one from each part) together. A spot weld failure criterion used for determining failure including shear and axial stresses acted on the spot weld, shell element size and spot weld location sensitivity scale factors and strain rate effect.

20 Claims, 8 Drawing Sheets

U.S. PATENT DOCUMENTS

| | | | |
|---|---|---|---|
| 2007/0090165 A1* | 4/2007 | Kumagai | 228/101 |
| 2007/0199924 A1* | 8/2007 | Yoshida et al. | 219/109 |
| 2007/0295700 A1* | 12/2007 | Nutwell et al. | 219/109 |
| 2010/0131256 A1* | 5/2010 | Hallquist | 703/8 |
| 2010/0145662 A1* | 6/2010 | Teng et al. | 703/1 |

FOREIGN PATENT DOCUMENTS

| | | | |
|---|---|---|---|
| JP | 2005326401 A | * | 11/2005 |
| JP | 2008107322 A | * | 5/2008 |

OTHER PUBLICATIONS

D. Radaj: "Structural stress, notch stress intensity factor approach for assessment of fatigue strength of spot welded joints", Welding in the World, Elsevier/ International Institute of Welding Roissy, FR vol. 28 No. 1/2 Jan. 1, 2001, pp. 29-39 XP008109973 ISSN: 0043-2288.

European Patent Office: "The extended European search report for application No. 09011220.2-2302", Apr. 8, 2010.

* cited by examiner

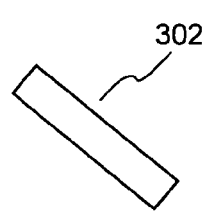
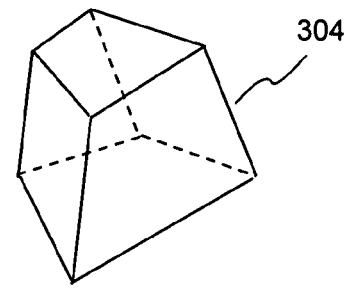
FIG. 3A  FIG. 3B
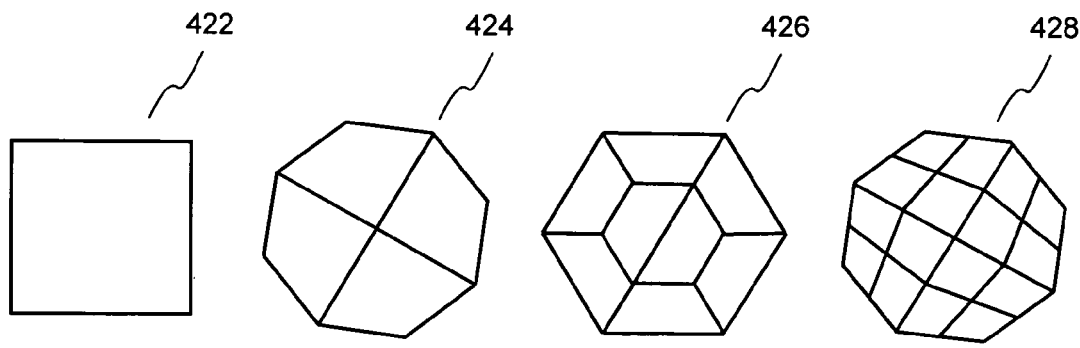
FIG. 4

SPOT WELD FAILURE DETERMINATION METHOD IN A FINITE ELEMENT ANALYSIS

FIELD OF THE INVENTION

The present invention generally relates to computer-aided engineering analysis of a structure (e.g., car, airplane), more particularly to a spot weld failure determination method in a finite element analysis.

BACKGROUND OF THE INVENTION

Finite element analysis (FEA) is a computer implemented method widely used in industry to model and solve engineering problems relating to complex systems such as three-dimensional non-linear structural design and analysis. FEA derives its name from the manner in which the geometry of the object under consideration is specified. With the advent of the modern digital computer, FEA has been implemented as FEA software. Basically, the FEA software is provided with a model of the geometric description and the associated material properties at each point within the model. In this model, the geometry of the system under analysis is represented by solids, shells and beams of various sizes, which are called elements. The vertices of the elements are referred to as nodes. The model is comprised of a finite number of elements, which are assigned a material name to associate with material properties. The model thus represents the physical space occupied by the object under analysis along with its immediate surroundings. The FEA software then refers to a table in which the properties (e.g., stress-strain constitutive equation, Young's modulus, Poisson's ratio, thermo-conductivity) of each material type are tabulated. Additionally, the conditions at the boundary of the object (i.e., loadings, physical constraints, etc.) are specified. In this fashion a model of the object and its environment is created.

FEA is becoming increasingly popular with automobile manufacturers for optimizing both the aerodynamic performance and structural integrity of vehicles. Similarly, aircraft manufacturers rely upon FEA to predict airplane performance long before the first prototype is ever developed. One of the popular FEA tasks is to simulate an impact event such as car crash. A problem associated with crashworthiness simulation is to properly simulate spot welds used for connecting two parts (e.g., sheet metal) in a structure.

Spot welding is a type of resistance welding used to weld various sheet metal products. Typically the sheets are in the 0.5-3.0 mm thickness range. The process uses two shaped copper alloy electrodes to concentrate welding current into a small "spot" and to simultaneously clamp the sheets together. One of the most common applications of spot welding is in the automobile manufacturing industry, where it is used almost universally to weld the sheet metal to form a car.

In a typical car, there are about 4,000-8,000 spot welds connecting 300-600 body parts to form the vehicle structure. For accurate simulation of the vehicle as a whole, those spot welds have to be modeled accurately. Spot welds are typically placed 2-3 centimeters apart, and each spot weld has a diameter between 4 to 9 millimeters (mm). Traditionally, each of the spot welds has been modeled with a very short beam element (e.g., length of 1-2 millimeters) in FEA. For example, in the 1990s, spot welds were modeled using two-node rigid bodies with the requirement that the nodal locations of the spot weld parts be at the physical location of the spot weld. This prior art approach required much work in creating the FEA model due to the effort to properly locate nodal points precisely at the weld locations. As the modern computer improves, the finite element models representing a vehicle have become huge (e.g., more than 4,000,000 elements varying in size from 2-4 mm). Thereby, the size of elements around the spot welds becomes smaller than the spot weld diameter. Representing spot welds using beam elements are not adequate any more, instead solid elements are used. In certain cases, spot welds have been modeled with more than one solid element. Furthermore, in a car crashworthiness simulation, spot weld failure needs to be considered and determined. The spot weld failure determination method for beam element has been well established. However, this method is inconsistent with traditional material failure method used in solid elements.

Therefore, it would be desirable to have an improved method for determining spot weld failure in a finite element analysis regardless which type of element is used for representing spot welds.

BRIEF SUMMARY OF THE INVENTION

This section is for the purpose of summarizing some aspects of the present invention and to briefly introduce some preferred embodiments. Simplifications or omissions in this section as well as the abstract and the title herein may be made to avoid obscuring the purpose of the section. Such simplifications or omissions are not intended to limit the scope of the present invention.

The present invention discloses a system, method and software product for determining spot weld failure in a finite element analysis of a structure such as an automobile. According to one aspect of the present invention, each spot weld in a structure is represented by a cluster of at least one solid element in a finite element analysis model of the structure. Each spot weld is used for tying together two parts (e.g., sheet metal parts). Each of the two parts are generally represented or modeled as a number of two-dimension shell elements. Since the tie-connection between the spot weld and the two parts can be located arbitrarily within the respective part, the shell elements representing the two parts do not have to be aligned in space. The only requirement is the two shell elements must overlap each other such that the spot weld can tie the two shell elements (i.e., one from each part) together.

According to another aspect of the present invention, a spot weld failure criterion used for determining spot weld failure including shear and axial stresses acting on the spot weld, shell element size and spot weld location sensitivity scale factors and strain rate effect. The failure criterion used herein is for "plug rupture" mode, in which the sheet metal around the spot weld nugget fails or ruptures.

In yet another aspect, the present invention is configured to treat each cluster as a whole, even though each cluster may contain more than one solid elements. For each cluster, one resultant set of shear and axial stresses is calculated in each solution cycle of a time-marching simulation. The resultant shear and axial forces are checked using the spot weld failure criterion.

According to one embodiment, the present invention is a method of determining spot weld failure in a time-marching simulation of a structure impact event for designing a structure. The method includes at least the following steps: receiving one or more spot weld definitions in a structure, each of the spot weld definitions includes a spot weld along with first and second parts connected therewith; creating a finite element analysis model of the structure including a cluster of at least one solid element to represent the spot weld, a plurality of first shell elements to represent the first part, and a plurality of second shell elements to represent the second part, said cluster having first and second ends, the first end having a plurality of nodes each connecting to corresponding one of the first shell elements and the second end having a plurality of nodes each connecting to corresponding one of the second shell elements; determining an overall axial stress sensitivity scale factor and an overall shear stress sensitivity scale factor for each end of the first and second ends; determining an overall location sensitivity scale factor of said each end of the first and second ends; calculating force and moment resultants at said each end in current solution cycle; calculating an overall plastic strain rate at said each end using plastic strain calculated in the current solution cycle and stored plastic strain in previous solution cycle of the time-marching simulation; checking spot weld failure criterion at said each end, in which the calculated force and moment resultants, the plastic strain rate, and the overall axial stress, overall shear stress and overall location sensitivity scale factors are used; and when the spot weld failure criterion indicates failure or rupture of the spot weld at either end of the first and second ends of the cluster, removing the cluster from the finite element analysis model for future solution cycles of the time-marching simulation.

According to another embodiment, the method further includes determining a plurality of individual axial stress sensitivity scale factors and a plurality of individual shear stress sensitivity scale factors of each of the nodes of said each end; deriving the overall axial stress sensitivity scale factor by averaging all of the individual axial stress sensitivity scale factors at said each end; deriving the overall shear stress sensitivity scale factor by averaging all of the individual shear stress sensitivity scale factors at said each end; determining a plurality of individual location sensitivity scale factors of each of the nodes of said each end; and deriving the overall location sensitivity scale factor by averaging all of the individual location sensitivity scale factors at said each end.

According to yet another embodiment, the method further includes grouping said more than one solid elements by a unique spot weld identification; and deriving the force and moment resultants by totaling individual force and moment of all of said more than one solid elements in the cluster, when more than one solid elements are in the cluster. Additionally, the method further comprises calculating a plurality of individual plastic strain rates of each of the nodes of said each end; and deriving the overall plastic strain rate by averaging all of the individual plastic strain rates at said each end According to yet another embodiment, the method further comprises graphically displaying one or more results of the time-marching simulation to a monitor of a computing device such that the results can be visualized and understood for further design decision of said designing of the structure.

Other objects, features, and advantages of the present invention will become apparent upon examining the following detailed description of an embodiment thereof, taken in conjunction with the attached drawings.

BRIEF DESCRIPTION OF THE DRAWINGS

These and other features, aspects, and advantages of the present invention will be better understood with regard to the following description, appended claims, and accompanying drawings as follows:

FIG. 3A is a diagram showing an exemplary beam element that can be used for representing a spot weld in a finite element analysis, according to an embodiment of the present invention;

FIG. 3B is a diagram showing an exemplary solid element that can be used for representing a spot weld in a finite element analysis, according to another embodiment of the present invention;

FIG. 4 is a diagram showing top view of four different solid element clusters, each may be used for representing a spot weld in accordance with one embodiment of the present invention;

DETAILED DESCRIPTION

Figure 1A:
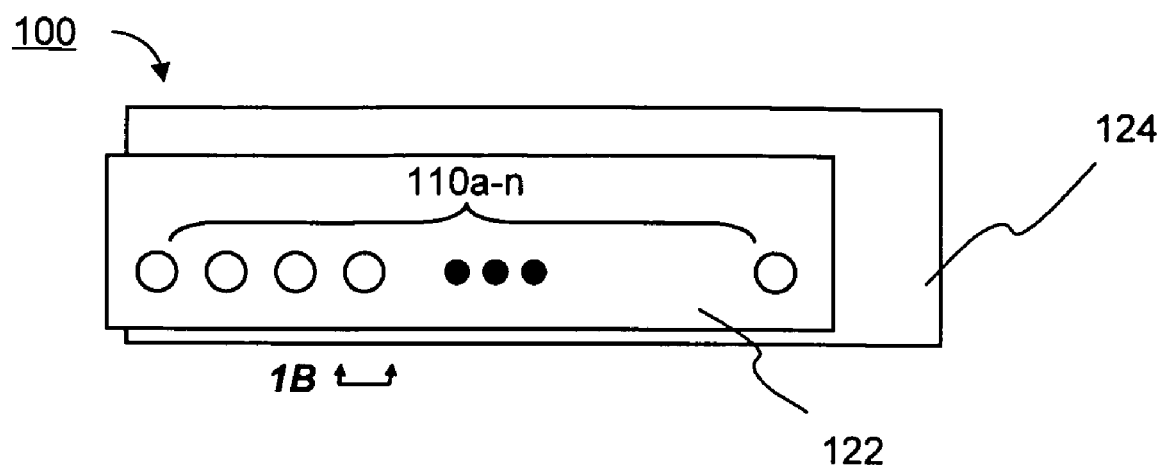
FIG. 1A is a top view of a group of spot welds used for connecting two sheet metal parts in a structure.

In the following description, numerous specific details are set forth in order to provide a thorough understanding of the present invention. However, it will become obvious to those skilled in the art that the present invention may be practiced without these specific details. The descriptions and representations herein are the common means used by those experienced or skilled in the art to most effectively convey the substance of their work to others skilled in the art. In other instances, well-known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

To facilitate the description of the present invention, it deems necessary to provide definitions for some terms that will be used throughout the disclosure herein. It should be noted that the definitions following are to facilitate the understanding and describe the present invention according to an embodiment. The definitions may appear to include some limitations with respect to the embodiment, the actual meaning of the terms has applicability well beyond such embodiment, which can be appreciated by those skilled in the art:

FEA stands for Finite Element Analysis.

Implicit FEA or solution refers to K u=F, where K is the effective stiffness matrix, u is the unknown displacement array and F is the effective loads array. F is a right hand side loads array while K is a left hand side stiffness matrix. The solution is performed at the global level with a factorization of the effective stiffness matrix, which is a function of the stiffness, mass and damping. One exemplary solution method is the Newmark time integration scheme.

Explicit FEA refers to M a=F, where "M" is the diagonal mass array, "a" is the unknown nodal acceleration array and "F" is the effective loads array. The solution can be carried out at element level without factorization of a matrix. One exemplary solution method is called the central difference method.

Time-marching simulation or time-domain analysis refers to an engineering analysis simulation in time domain, for example, a simulation of car crashworthiness using a finite element analysis in time domain.

Beam element refers to a one-dimensional finite element defined by two end nodes. The beam carries an axial stress and three shear stresses that may vary across the cross section, when the beam is under straining force. Axial strain of the beam is defined as amount of stretch in the axial direction of the beam. For example, when a beam is stretched from original length L to an elongated length (L+δ) by a tension axial force, the axial strain ε is defined as the total elongation δ per unit length (i.e., ε=δ/L).

Shell element refers to a two-dimensional element defined by an area, for example, a triangular element, a quadrilateral element, etc.

Solid element refers to a three-dimensional volumetric finite element, for example, a 4-node tetrahedral element, an 8-node hexahedral element, etc.

Strain refers to a non-dimensional quantity derived from measuring the deformation of a sample or specimen.

Nodal strain refers to strain at each node of a finite element (e.g., shell element), which represents or models portion of a structure.

Plastic strain refers to non-recoverable strain after removing the load from a specimen or sample.

Plastic nodal strain $\epsilon_p$ refers to plastic strain at a node of a finite element (e.g., shell element).

Embodiments of the present invention are discussed herein with reference to FIGS. 1A-8. However, those skilled in the art will readily appreciate that the detailed description given herein with respect to these figures is for explanatory purposes as the invention extends beyond these limited embodiments.

Figure 1B:
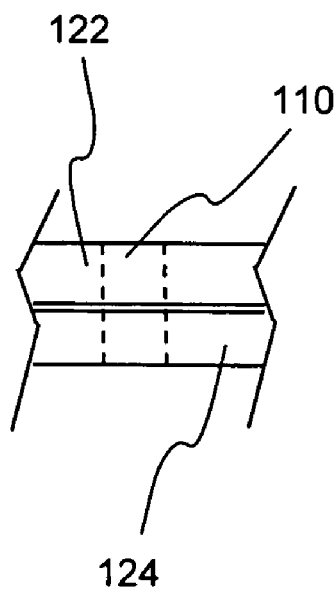
FIG. 1B is an elevation view of a representative one of the spot welds of FIG. 1A.

Referring first to FIG. 1A, a top view of an exemplary structure 100 using a number of spot welds to connect two parts is shown. The structure 100 includes a first part (e.g., top plate 122) and a second part (e.g., bottom plate 124) connected by a number of spot welds 110a-n. FIG. 1B shows an elevation of one typical representative spot weld 110 and connected the top 122 and bottom plates 124 of the structure 100. To avoid illustration complexity, the relatively simple exemplary structure 100 is used. The present invention can be applied to complex structures such as automobiles, airplanes, etc.

Figure 2A:
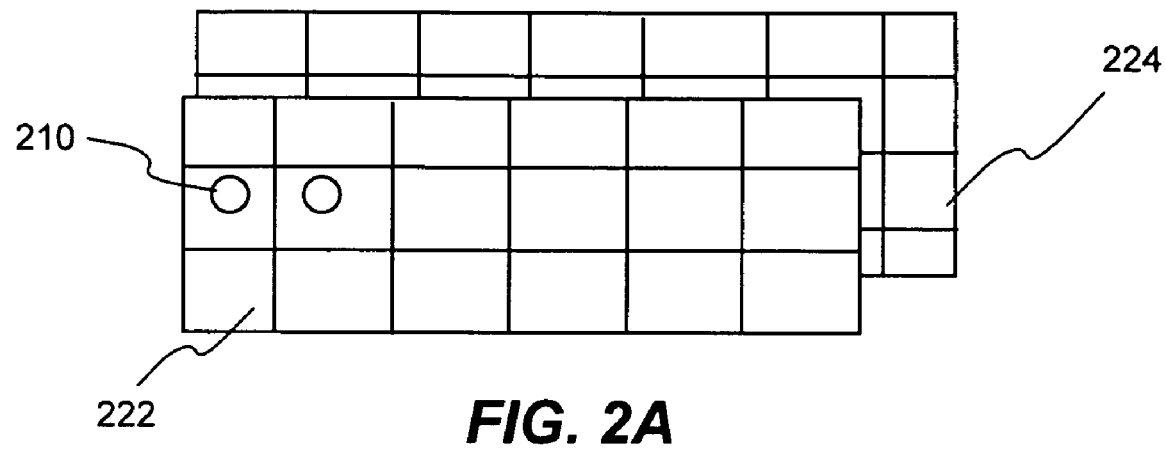
FIG. 2A is a top view of a finite element analysis model of the structure of FIGS. 1A-B.
Figure 2B:
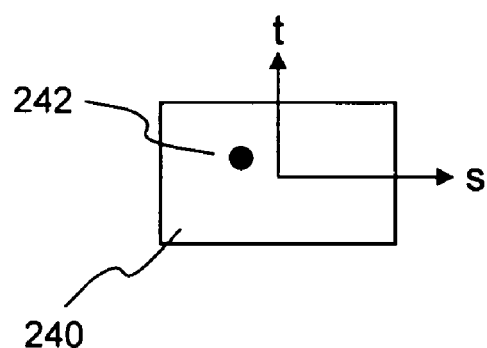
FIG. 2B is a diagram showing an exemplary location of a spot weld relative to one of the connected shell element.

An exemplary finite element model of the structure 100 of FIG. 1 is shown in FIG. 2A. The top plate 122 is represented by a first finite element mesh 222 comprising a plurality of shell elements, while the bottom plate 124 represented by a second finite element mesh 224. Each of the spot welds 110a-n is represented by a special spot weld element 210 (two shown in FIG. 2) that ties two parts together. There is no restriction as to where the cluster can be located relative to the connected shell elements. FIG. 2B shows an exemplary shell element 240 with a spot weld connection 242. The position of the spot weld 242 does not have to be located on the corner or edge of the element 242. To track the location of the spot weld connection within a connected shell element, a set of element parametric coordinate (s, t) is used for each connected shell element with every spot weld. In other words, each end of a spot weld is associated with a parametric coordinate of the connected shell element.

The spot weld element 210 can be either a beam element 302 shown in FIG. 3A or a cluster of at least one solid element 304 in FIG. 3B. The present invention includes a method of determining spot weld failure regardless which element has been chosen.

When spot weld 110 is modeled or represented by beam element, it is a one-to-one relationship. Two ends of a beam element correspond to two ends of the spot weld tying to the two parts. For example, two ends of spot weld 110 are top and bottom plates 122 and 124.

When spot weld is represented by a cluster of at least one solid element, there are many choices. The most common selections are shown in FIG. 4, which includes top view for four exemplary options. The first option 422 is a one-element cluster. Second 424, third 426 and fourth 428 options are 4-, 8-, and 16-element cluster, respectively. Each of these exemplary clusters consists of one layer of element connecting two shell elements of the two connected parts (i.e., top and bottom plates 122, 124). In one aspect of the present invention, the area of a spot weld (generally a circular shape) is preserved when represented or modeled by a cluster of solid elements. For example, area of the first option 422 (a square area) is set to be equal to the area of the corresponding spot weld. If the first option 422 comprises a square shape. Each side would have a length equal to $$\frac{\sqrt{\pi}}{2}d,$$

where d is diameter of the spot weld. A plan view shown an exemplary spot weld is in FIG. 5B.

When performing a non-linear time-marching simulation of impact analysis (e.g., car crashworthiness), it is critical to determine which component represented by one or more finite elements has reached a failure state. For spot weld, there are two types of failure mode. One is referred to as "plug rupture failure", in which the sheet metal around the spot weld nugget or plug ruptures or fails. The other is referred to as "nugget failure or rupture", in which the spot weld itself fails. Due to applications of the present invention, only the "plug rupture" mode of failure is checked. To determine "plug rupture" failure, a beam theory based spot weld failure criterion is used. For example, an exemplary failure criterion of a spot weld is listed as follows:

$$\left(\frac{\sigma_{rr}}{\sigma_{rr}^F(\varepsilon^p)}\right)^2 + \left(\frac{\tau}{\tau^F(\varepsilon^p)}\right)^2 \geq 1 \qquad \text{Eq. (1)}$$

-continued $$\sigma_{rr}^F(\dot{\varepsilon}^p) = \sigma_{rr}^F\left[1 + \left(\frac{\dot{\varepsilon}^p}{C}\right)^{\frac{1}{p}}\right] \quad \text{Eq. (2a)}$$

$$\tau^F(\dot{\varepsilon}^p) = \tau^F\left[1 + \left(\frac{\dot{\varepsilon}^p}{C}\right)^{\frac{1}{p}}\right] \quad \text{Eq. (2b)}$$

$$\sigma_{rr} = \frac{N_{rr}}{A} + \frac{\sqrt{M_{rs}^2 + M_{rt}^2}}{\alpha Z} \quad \text{Eq. (3a)}$$

$$\tau = \frac{M_{rr}}{2Z} + \frac{\sqrt{N_{rs}^2 + N_{rt}^2}}{A} \quad \text{Eq. (3b)}$$

$$A = \pi\frac{d^2}{4} \quad \text{Eq. (3c)}$$

$$Z = \pi\frac{d^3}{32} \quad \text{Eq. (3d)}$$

where:

$\sigma_{rr}$ and $\tau$ are axial and shear stresses of the spot weld, respectively;

$\sigma_{rr}^F(\dot{\varepsilon}^p)$ and $\tau^F(\dot{\varepsilon}^p)$ are the spot weld rupture or failure stress in tension and shear including the strain rate effect (e.g., based on Cowper-Symonds model), respectively;

$\sigma_{rr}^F$ and $\tau^F$ are the static spot weld rupture or failure stress in tension and shear determined by a specimen test;

C and p are material dependent strain rate parameters of the Cowper-Symonds model used for scaling the static rupture stress obtained in the specimen test;

$\dot{\varepsilon}^p$ is the plastic strain rate;

$N_{rr}$ is the axial force resultant of the spot weld;

$N_{rs}$ and $N_{rt}$ are the shear force resultants in the r and t directions, respectively;

$M_{rr}$ is the torsion resultant of the spot weld;

$M_{rs}$ and $M_{rt}$ are the moment resultants with respect to the 's' and 't' axes of the spot weld, respectively;

A is the area of the spot weld;

Z is the section modulus of the spot weld; and d is the diameter of the spot weld; and α is a user defined scale factor with a default value of one.

The spot weld is determined to be ruptured when Equation (1) is satisfied. The plastic strain rate is determined from each of the connected shell elements. Parameters C and p are material dependent. The failure criterion is calculated independently for each end of the spot weld (i.e., each surface of the cluster). Equations (2a) and (2b) are corrections to account for material property variation in terms of energy absorption in an impact event (i.e., car crash). The material property (e.g., stress-strain characteristics) is sensitive to the strain rate. Therefore, the property such as failure or rupture stress obtained in a specimen testing needs to be modified or scaled to reflect the dynamic effect (i.e., strain rate effect). In the Cowper-Symonds model (e.g., Equations (2a) and (2b)), the strain rate for car or vehicle collision has a range between 0.1 and 100 per second. Parameters C and p are material dependent and can be determined from empirical data with known methods, for example, least squares fit.

Figure 5A:
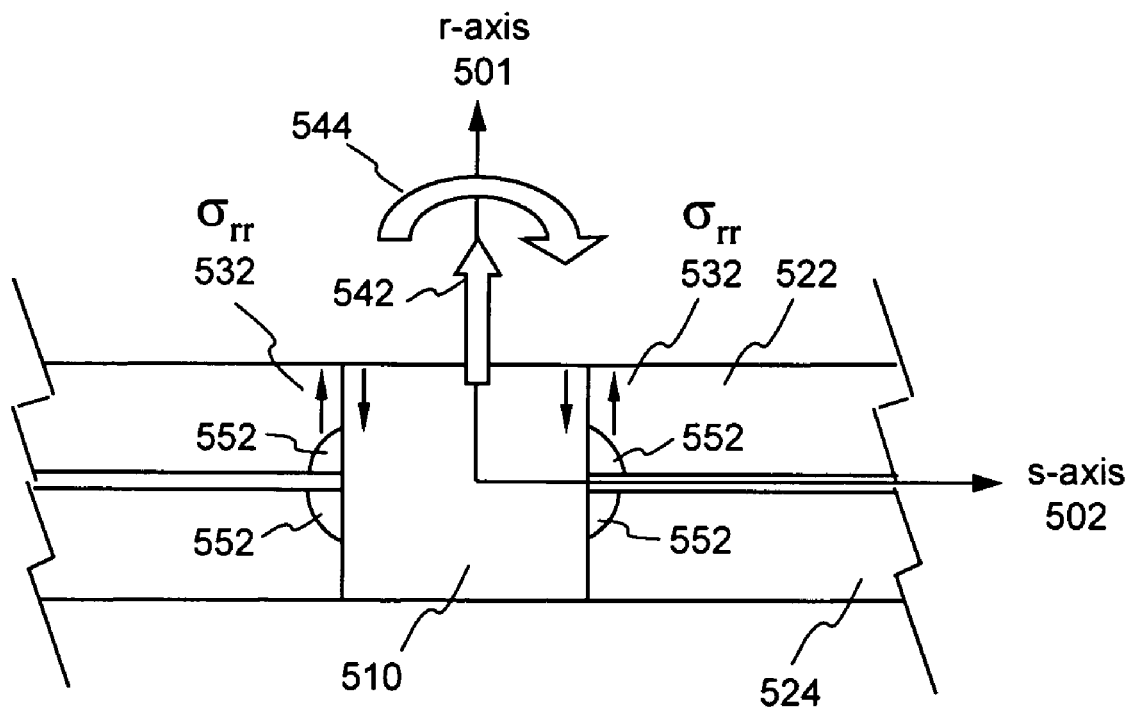
FIG. 5A is a diagram showing cross tension in a spot weld.
Figure 5B:
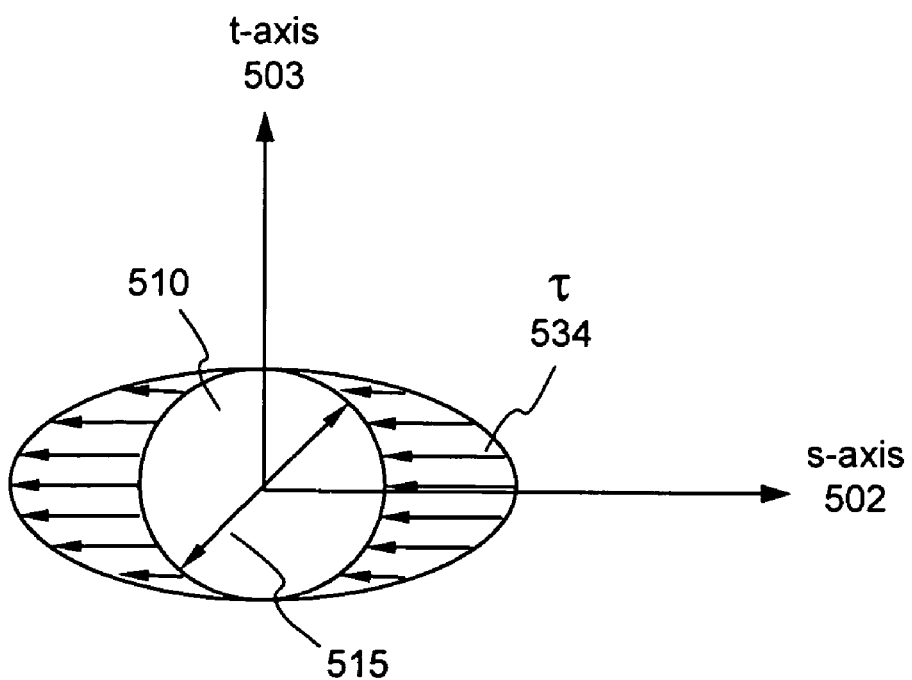
FIG. 5B is a diagram showing shear force in a spot weld.

FIG. 5A shows spot weld tension or axial stress $\sigma_{rr}$ 532 in an elevation view of a spot weld 510 with connected top 522 and bottom plates 524. Spot weld shear stress $\tau$ 534 is shown in a plan view of the spot weld in FIG. 5B. The coordinate system (r, s, t) used in Equations (3a-d) is shown as the r-axis 501 (i.e., axial direction of the spot weld) and the s-axis 502 and the t-axes 503 (i.e., two radial directions of the spot weld). Also shown in FIG. 5B is the diameter d 515 of the exemplary circular shape spot weld. The area A of the spot weld can be calculated using Equation (3c). Force resultant 542 is the total axial force acting on the spot weld 510, while moment resultant 544 is the total moment. The force and moment resultants 542 and 544 can be derived using known methods, for example, integrating axial stress 532 along the perimeter of the spot weld 510 would result in a force resultant 542. Moment resultant 544 can be calculated using a moment arm from the center to the perimeter of the spot weld 510. Force 542 and moment 544 resultants are straightforward when the spot weld 510 is modeled with one element (e.g., a beam 302 of FIG. 3A or a solid element 422 of FIG. 4). For spot welds modeled with multiple solid elements (e.g., clusters 424, 426 and 428 of FIG. 4), force 542 and moment 544 resultants needs to include components from all of the elements in a cluster.

Plastic strains 552 can develop when the force 542 and moment 544 resultants act on the spot weld 510 and connected plates (i.e., top 522 and bottom 524 plates) exceed the yield stress of the plates. These plastic strains 552 are calculated in each solution cycle of a time-march simulation.

While Equation (1) is adequate for determining the spot weld failure in theory, the experimental data have shown that predicting spot weld failure using finite element analysis is sensitive to at least two factors. The first factor is the location of the spot weld on the connected shell element (i.e., (s, t) coordinate of the spot weld on the shell element shown FIG. 2B). The second is the physical size of the shell element connected to the spot weld. To account for these two sensitive factors, the spot weld failure criterion is written to include additional scale factors as follows:

$$\left(\frac{S_T S_O \sigma_{rr}}{\sigma_{rr}^F(\dot{\varepsilon}^p)}\right)^2 + \left(\frac{S_S S_O \tau}{\tau^F(\dot{\varepsilon}^p)}\right)^2 \geq 1 \quad \text{Eq. (4)}$$

where:

$S_T$ is axial stress element size sensitivity scale factor 602, $S_S$ is a shear stress element size sensitivity scale factor 604, and $S_O$ is location sensitivity scale factor 606A-B for different location in which the spot weld is connected to the shell element.

Figure 6A:
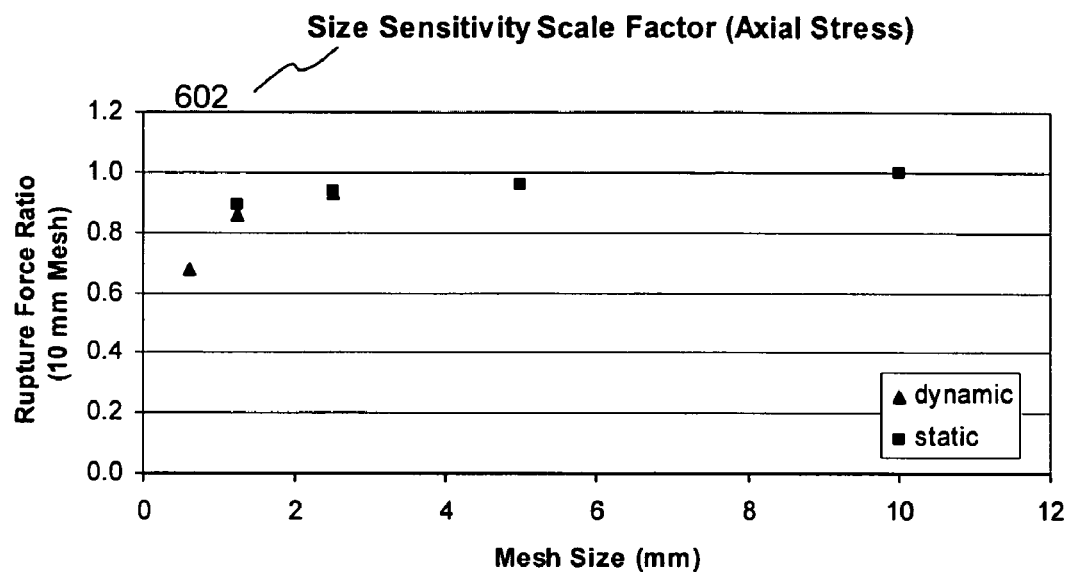
FIG. 6A is a X-Y chart showing finite element mesh size effect with respect to cross tension of a spot weld for determining spot weld failure, according to an embodiment of the present invention.
Figure 6B:
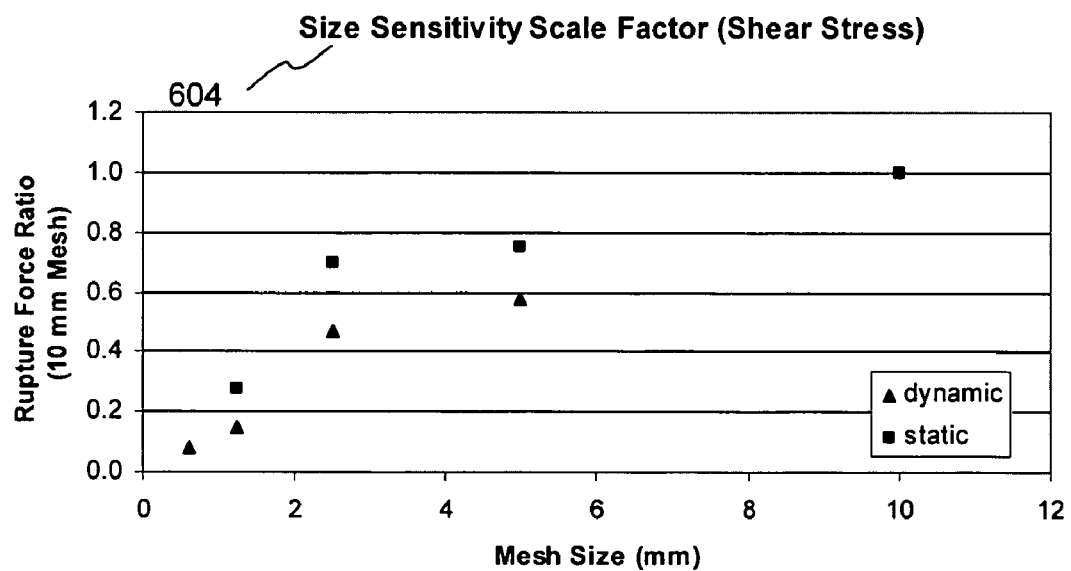
FIG. 6B is a X-Y chart showing the finite element mesh size effect with respect to shear force of a spot weld for determining spot weld failure, according to an embodiment of the present invention.

For the mesh size sensitivity, an exemplary set of cross tension or axial stress sensitivity scale factors 602 is shown in FIG. 6A for various sizes of shell element (i.e., size of finite element mesh), according to one embodiment of the present invention. Similarly, an exemplary set of shear stress sensitivity factors 604 for various sizes of shell element is shown in FIG. 6B. There are two sets of data in FIGS. 6A-B, one for static axial and shear forces, the other for dynamic. In one embodiment, an average value can be used. In another embodiment, one of them can be used depending upon nature of the force in a simulation. Both sets of data are calibrated to a 10×10 mm shell element. In other words, the scale factor for a 10×10 mm shell element is 1.0, while other sizes of elements need to adjust in accordance with the data in FIGS. 6A-B.

Figure 6C:
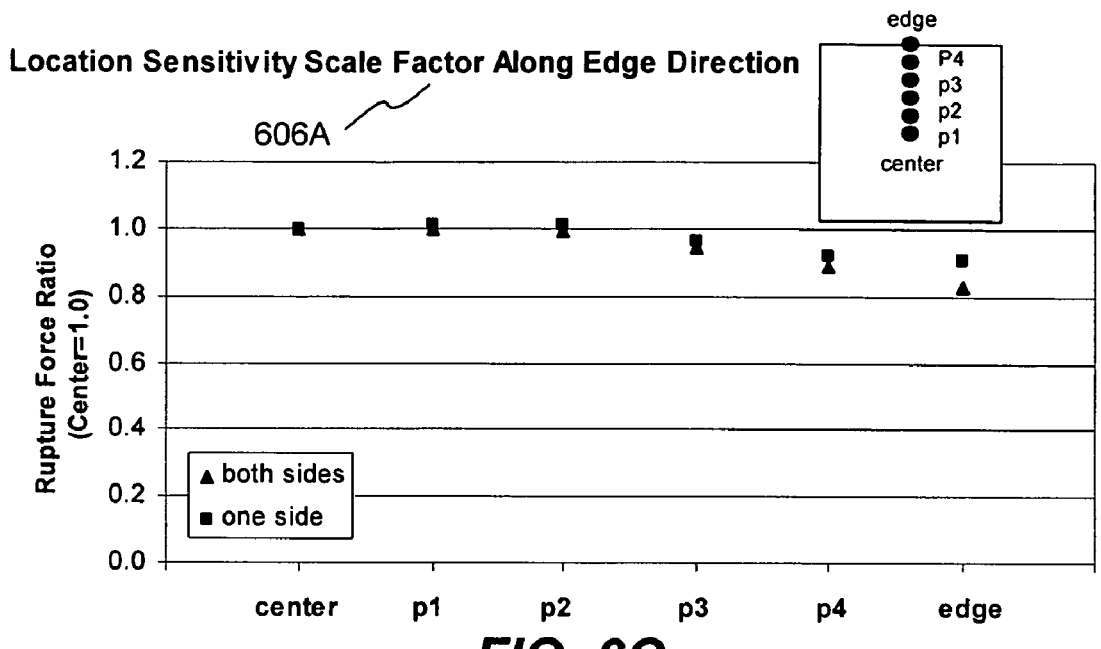
FIGS. 6C and 6D are two X-Y charts showing the spot weld location with respect to the connected shell element for determining spot weld failure in accordance with one embodiment of the present invention.
Figure 6D:
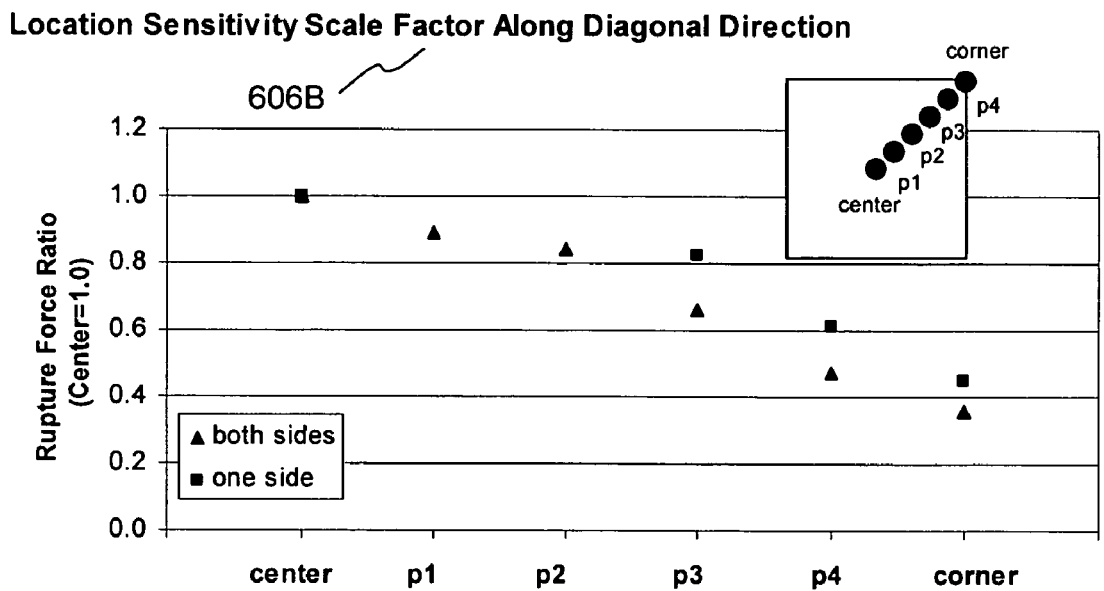

For the location sensitivity scale factor, FIG. 6C shows an exemplary set of location sensitivity scale factors 606A, which are for various locations in a direction from the center of the element to an edge. FIG. 6D shows another exemplary set of location sensitivity scale factors 606B that are for various locations in a direction from the center of the element to a corner. There are two sets of data shown in FIGS. 6C-D, one for an element with spot welds connected at same relative location (denoted as both sides), while the other is for an element with spot welds connected at different relative location (denoted as one side).

Figure 7:
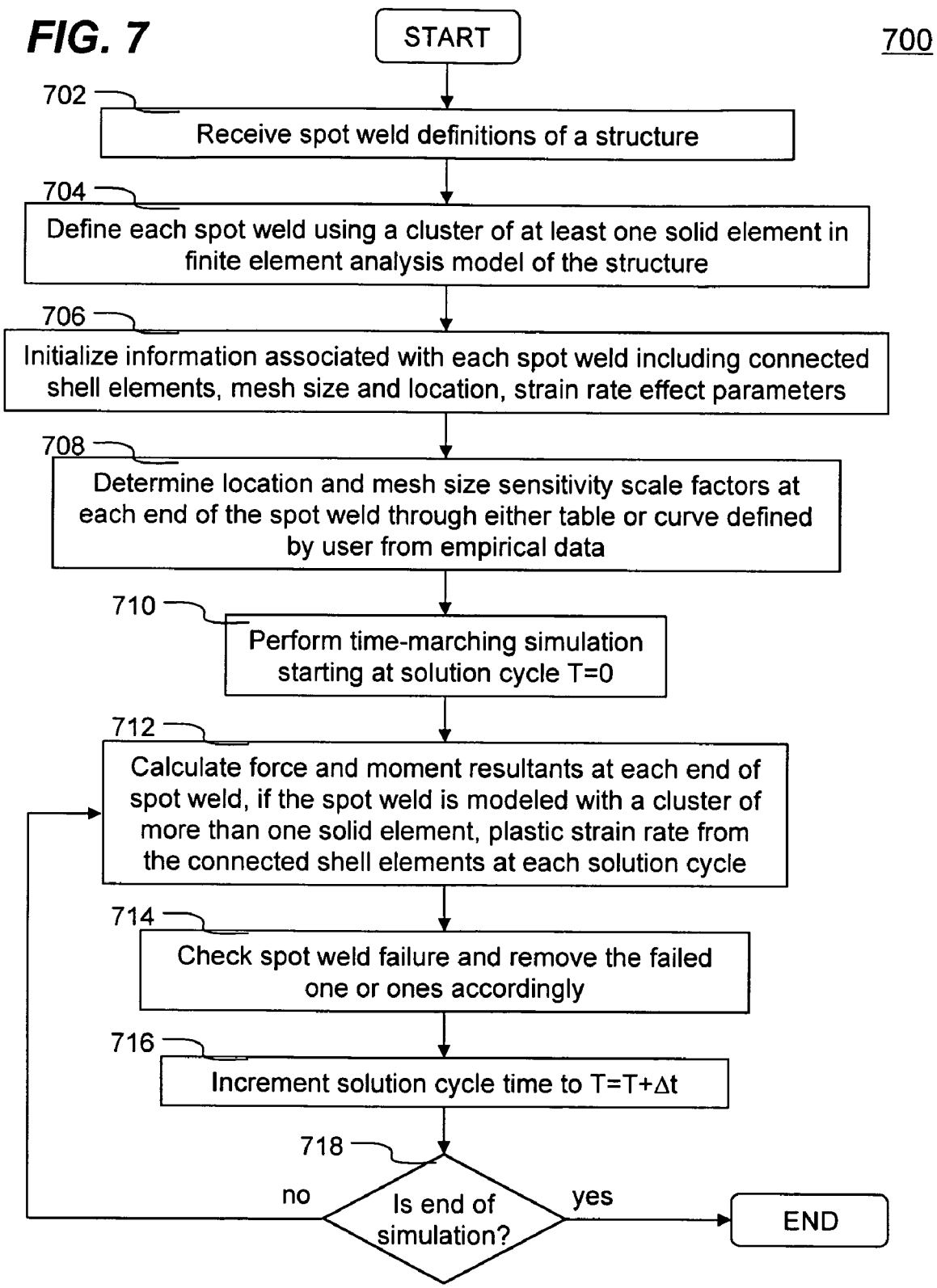
FIG. 7 is a flowchart illustrating an exemplary process of determining spot weld failure in a finite element analysis when spot welds are represented or modeled using a cluster of one or more solid elements, according to an embodiment of the present invention.

FIG. 7 is a flowchart illustrating an exemplary process 700 of determining spot weld failure in a finite element analysis of a structure with spot weld connections contained therein, according to one embodiment of the present invention. The process 700 may be implemented in software and preferably understood in conjunction with previous figures.

Process 700 starts by receiving one or more spot weld definitions of a structure at step 702. For example, the location and orientation of each spot weld in an automobile. Additionally, information of the two connected parts for each spot weld is also received. The received spot weld definitions is fed into a finite element analysis software module (loaded on a computer's memory as described in descriptions associated with FIG. 8 below) either directly or indirectly via well known methods. An exemplary well known method is to utilize a pre-processing software module with graphic user interface. Another well known method is to manually enter the received spot weld definitions according to a predefined input format of the finite element analysis (FEA) software module.

Next, at step 704, each spot weld is represented either by a single beam element or a cluster of at least one solid element using the received spot weld definitions. This is generally performed by either the pre-processing software module or the FEA software module with implicit or explicit directive from users (i.e., engineer conducting car crash simulation). When there are more than one solid elements in a cluster, the related solid elements are grouped together with a known technique such as mark related solid elements with a spot weld identification (Spot weld ID). The grouping of the related solid elements can ensure future computation properly (e.g., calculating force and moment resultants at either end of a spot weld). Then, at step 706, information associated with each spot weld is initialized in the FEA software module. The initialized information includes the connected shell element (e.g., unique shell element no. or ID), material strain rate effect parameters (e.g., parameter C and p), FEA mesh size and spot weld parametric coordinate in the connected shell element at two ends of the spot weld.

The material strain rate parameters C and p are assigned at each node of either end of spot weld, and then converted to a single number using known techniques such as simple or weighed average. The material strain rate parameters C and p are based on the sheet metal parts (represented by shell elements) connected at corresponding end of the spot weld. For example, in FIG. 4, a cluster of single solid element 422 consists of four nodes at each end. One method is to compute C and p at four nodes and use simple average to come up with a single set of C and p for the spot weld in determination of spot weld failure. The four nodes of the cluster may be located on four different shell elements, each element representing different material thus each having different values of C and p. In another example, for a more complex cluster of eight solid elements 426, there are twelve nodes involved in the calculation of C and p. Instead of using simple average of the twelve sets of C and p, the outer nodes and inner nodes may be assigned different weighting factors for a weighted average calculation.

Using the initialized and input information at step 708, the spot weld location and mesh size sensitivity scale factors (e.g., $S_O$, $S_T$ and $S_S$ of Equation (4)) can be determined from empirical tables or charts predefined by the users, for example, X-Y charts shown in FIGS. 6A-6D.

After input and initialization are completed, the FEA software module starts time-marching simulation of impact event of interest (e.g., car crash or vehicle collision) at step 710. The time-marching simulation usually starts at an initial solution cycle (i.e., a solution cycle corresponds to time t=0). The time-marching or time-domain simulation is performed in one of the well-known procedures, for example, explicit non-linear finite element analysis. At step 712, force and moment resultants are calculated at each end of every spot weld if the cluster comprises more than one solid element. If there is only one element (beam or solid), the force and moment resultants are directly available at the end of each solution cycle. The force and moment resultants are then converted to axial and shear stresses. As for the plastic strain rate calculation, at each spot weld node, the plastic strain rate $\dot{\varepsilon}^p$ can be calculated as follows:

$$\dot{\varepsilon}^p = \frac{\varepsilon^{p(n+1)} - \varepsilon^{p(n)}}{\Delta t} \quad \text{Eq. (5)}$$

where:
$\varepsilon^{p(n)}$ is nodal plastic strain at previous solution cycle (n);
$\varepsilon^{p(n+1)}$ is nodal plastic strain at current solution cycle (n+1); and
$\Delta t$ is the time increment between the previous (n) and current solution cycle (n+1).
Nodal plastic strain (e.g., plastic strain 522 of FIG. 5A) is then stored for future calculation (i.e., next solution cycle).

Axial and shear stresses (i.e., $\sigma_{rr}$ and $\tau$) of each spot weld are then calculated and spot weld failure is determined using Equation (4) at step 714. The spot weld is determined to be failed or ruptured is removed accordingly. The simulation time "t" is incremented by a time increment $\Delta t$ for the next solution cycle at step 716. At test 718, it is determined whether the time-marching simulation has completed (e.g., check against a predetermined total simulation time). If 'no', process 700 moves back to step 712 performing another solution cycle of the time-marching simulation until test 718 becomes 'yes' and, process 700 ends.

According to one aspect of the present invention, process 700 enables same determination of spot weld failures whether the spot weld is modeled or represented by a beam element or a cluster of solid elements. One of the advantages is to allow spot welds be modeled in a combination of beam elements and clusters of solid elements. Only those spot welds required more detail results are modeled with solid elements.

Figure 8:
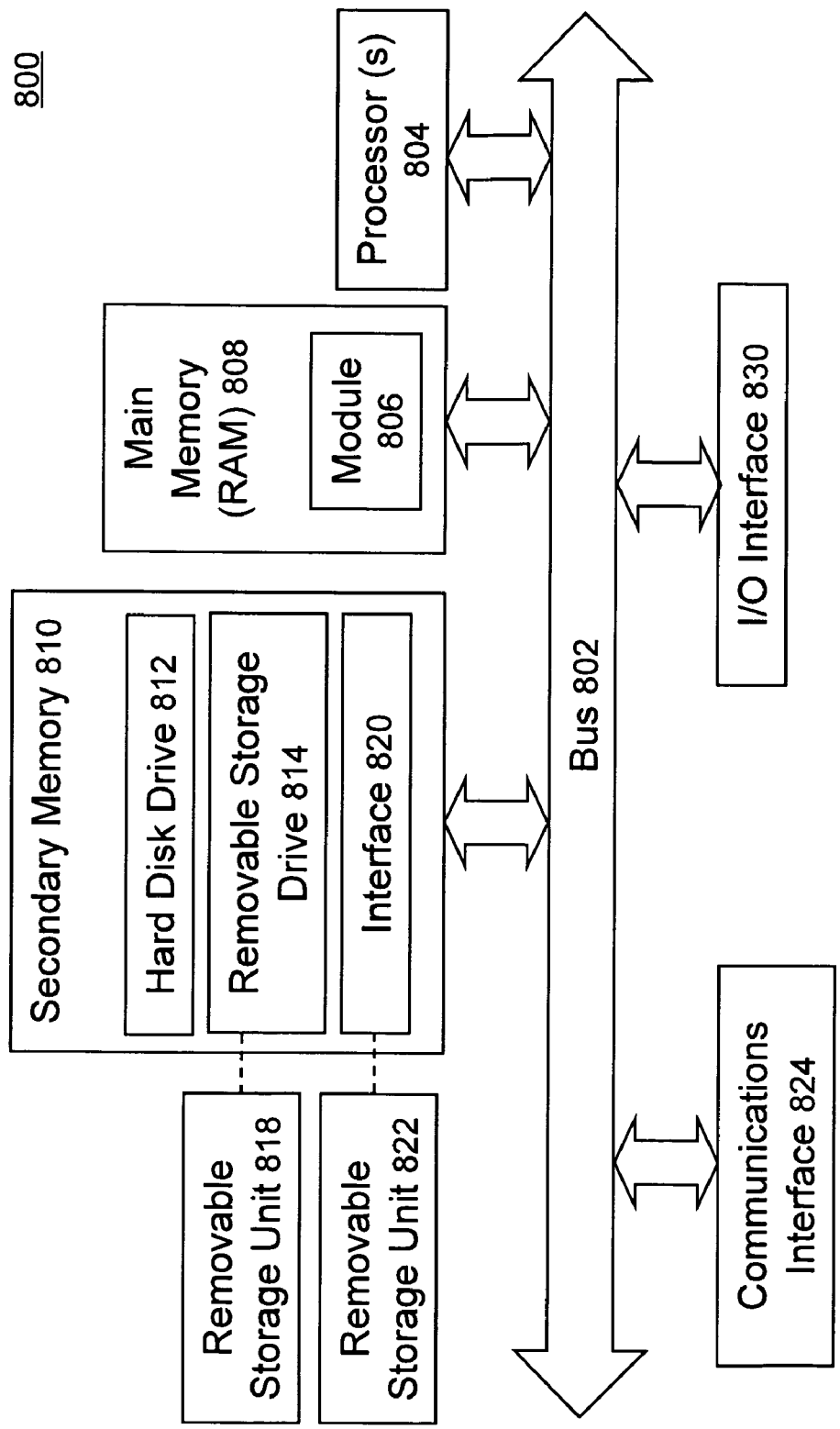
FIG. 8 is a function diagram showing salient components of a computing device, in which an embodiment of the present invention may be implemented.

According to one aspect, the present invention is directed towards one or more computer systems capable of carrying out the functionality described herein. An example of a computer system 800 is shown in FIG. 8. The computer system 800 includes one or more processors, such as processor 804. The processor 804 is connected to a computer system internal communication bus 802. Various software embodiments are described in terms of this exemplary computer system. After reading this description, it will become apparent to a person skilled in the relevant art(s) how to implement the invention using other computer systems and/or computer architectures.

Computer system 800 also includes a main memory 808, preferably random access memory (RAM), and may also include a secondary memory 810. The secondary memory 810 may include, for example, one or more hard disk drives 812 and/or one or more removable storage drives 814, representing a floppy disk drive, a magnetic tape drive, an optical disk drive, etc. The removable storage drive 814 reads from and/or writes to a removable storage unit 818 in a well-known manner. Removable storage unit 818, represents a floppy disk, magnetic tape, optical disk, etc. which is read by and written to by removable storage drive 814. As will be appreciated, the removable storage unit 818 includes a computer usable storage medium having stored therein computer software and/or data.

In alternative embodiments, secondary memory 810 may include other similar means for allowing computer programs or other instructions to be loaded into computer system 800. Such means may include, for example, a removable storage unit 822 and an interface 820. Examples of such may include a program cartridge and cartridge interface (such as that found in video game devices), a removable memory chip (such as an Erasable Programmable Read-Only Memory (EPROM), Universal Serial Bus (USB) flash memory, or PROM) and associated socket, and other removable storage units 822 and interfaces 820 which allow software and data to be transferred from the removable storage unit 822 to computer system 800. In general, Computer system 800 is controlled and coordinated by operating system (OS) software, which performs tasks such as process scheduling, memory management, networking and I/O services.

There may also be a communications interface 824 connecting to the bus 802. Communications interface 824 allows software and data to be transferred between computer system 800 and external devices. Examples of communications interface 824 may include a modem, a network interface (such as an Ethernet card), a communications port, a Personal Computer Memory Card International Association (PCMCIA) slot and card, etc. Software and data transferred via communications interface 824 are in the form of signals 828 which may be electronic, electromagnetic, optical, or other signals capable of being received by communications interface 824. The computer 800 communicates with other computing devices over a data network based on a special set of rules (i.e., a protocol). One of the common protocols is TCP/IP (Transmission Control Protocol/Internet Protocol) commonly used in the Internet. In general, the communication interface 824 manages the assembling of a data file into smaller packets that are transmitted over the data network or reassembles received packets into the original data file. In addition, the communication interface 824 handles the address part of each packet so that it gets to the right destination or intercepts packets destined for the computer 800. In this document, the terms "computer program medium" and "computer usable medium" are used to generally refer to media such as removable storage drive 814, and/or a hard disk installed in hard disk drive 812. These computer program products are means for providing software to computer system 800. The invention is directed to such computer program products.

The computer system 800 may also include an input/output (I/O) interface 830, which provides the computer system 800 to access monitor, keyboard, mouse, printer, scanner, plotter, and alike.

Computer programs (also called computer control logic) are stored as application modules 806 in main memory 808 and/or secondary memory 810. Computer programs may also be received via communications interface 824. Such computer programs, when executed, enable the computer system 800 to perform the features of the present invention as discussed herein. In particular, the computer programs, when executed, enable the processor 804 to perform features of the present invention. Accordingly, such computer programs represent controllers of the computer system 800.

In an embodiment where the invention is implemented using software, the software may be stored in a computer program product and loaded into computer system 800 using removable storage drive 814, hard drive 812, or communications interface 824. The application module 806, when executed by the processor 804, causes the processor 804 to perform the functions of the invention as described herein.

The main memory 808 may be loaded with one or more application modules 806 that can be executed by one or more processors 804 with or without a user input through the I/O interface 830 to achieve desired tasks. In operation, when at least one processor 804 executes one of the application modules 806, the results are computed and stored in the secondary memory 810 (i.e., hard disk drive 812). The status of the finite element analysis (e.g., car crashworthiness, failure of spot weld) is reported to the user via the I/O interface 830 either in a text or in a graphical representation Although the present invention has been described with reference to specific embodiments thereof, these embodiments are merely illustrative, and not restrictive of, the present invention. Various modifications or changes to the specifically disclosed exemplary embodiments will be suggested to persons skilled in the art. For example, whereas spot weld location and mesh size sensitivity scale factors have been shown and described as static numbers only calculated once in the initialization stage. These scale factors may be determined at each solution cycle for different requirement. Furthermore, whereas the finite element analysis has been shown and described as car crash simulation, other types of impact events may also apply, for example, metal forming. In summary, the scope of the invention should not be restricted to the specific exemplary embodiments disclosed herein, and all modifications that are readily suggested to those of ordinary skill in the art should be included within the spirit and purview of this application and scope of the appended claims.

What is claimed is:

1. A method of determining spot weld failure in a time-marching simulation of a structure impact event for designing a structure with one or more spot welds contained therein, the method comprising:
   receiving one or more spot weld definitions in a structure, each of the spot weld definitions includes a spot weld along with first and second parts connected therewith;
   creating a finite element analysis model of the structure including a cluster of at least one solid element to represent the spot weld, a plurality of first shell elements to represent the first part, and a plurality of second shell elements to represent the second part, said cluster having first and second ends, the first end having a plurality of nodes each connecting to corresponding one of the first shell elements and the second end having a plurality of nodes each connecting to corresponding one of the second shell elements;
   determining an average axial stress sensitivity scale factor and an average shear stress sensitivity scale factor for each end of the first and second ends;
   determining an average location sensitivity scale factor of said each end of the first and second ends;
   calculating force and moment resultants at said each end in current solution cycle of the time-marching simulation;
   calculating an overall plastic strain rate at said each end using plastic strain calculated in the current solution cycle and stored plastic strain in previous solution cycle of the time-marching simulation;
   checking spot weld failure criterion at said each end in the current solution cycle, the spot weld failure criterion is a function of the calculated force and moment resultants, the plastic strain rate, and the average axial stress sensitivity scale factor, the average shear stress sensitivity scale factor and the average location sensitivity scale factor; and when the spot weld failure criterion indicates failure or rupture of the spot weld at either end of the first and second ends of the cluster, removing the cluster from the finite element analysis model for subsequent solution cycles of the time-marching simulation.

2. The method of claim 1, wherein the finite element analysis model is configured for representing an automobile in a crashworthiness analysis.

3. The method of claim 1, determining the average axial stress sensitivity scale factor and the average shear stress sensitivity scale factor for said each end, further comprises:

determining a plurality of individual axial stress sensitivity scale factors and a plurality of individual shear stress sensitivity scale factors of each of the nodes of said each end;

deriving the average axial stress sensitivity scale factor by averaging all of the individual axial stress sensitivity scale factors at said each end; and deriving the average shear stress sensitivity scale factor by averaging all of the individual shear stress sensitivity scale factors at said each end.

4. The method of claim 3, wherein each of the individual axial stress and shear sensitivity scale factors is configured to facilitate different shell element size corresponding to one of the shell elements that is connected to said each node of the nodes at said each end.

5. The method of claim 1, determining the average location sensitivity scale factor of said each end, further comprises:

determining a plurality of individual location sensitivity scale factors of each of the nodes of said each end; and deriving the average location sensitivity scale factor by averaging all of the individual location sensitivity scale factors at said each end.

6. The method of claim 5, wherein each of the individual location sensitivity scale factors is configured to facilitate different connection position corresponding to one of the first and second shell elements that is connected to said each node of the nodes at said each end.

7. The method of claim 1, further comprises graphically displaying one or more results of the time-marching simulation to a monitor of a computing device such that the results can be visualized and understood for further design decision of said designing of the structure.

8. The method of claim 1, calculating the force and moment resultants further comprises:

when more than one solid elements in the cluster,
grouping said more than one solid elements by a unique spot weld identification; and
deriving the force and moment resultants by totaling individual force and moment of all of said more than one solid elements in the cluster.

9. The method of claim 1, calculating the overall plastic strain rate at said each end further comprises:

calculating a plurality of individual plastic strain rates of each of the nodes of said each end; and
deriving the overall plastic strain rate by averaging all of the individual plastic strain rates at said each end.

10. The method of claim 9, wherein the plurality of plastic individual strain rates is based on the plastic strain of a corresponding one of the first and second shell elements that is connected to said each of the nodes.

11. A non-transitory computer-readable storage medium containing instructions for controlling a computer system to determining spot weld failure in a time-marching simulation of a structure impact event for designing a structure with one or more spot welds contained therein by a method comprising:

receiving one or more spot weld definitions in a structure, each of the spot weld definitions includes a spot weld along with first and second parts connected therewith;

creating a finite element analysis model of the structure including a cluster of at least one solid element to represent the spot weld, a plurality of first shell elements to represent the first part, and a plurality of second shell elements to represent the second part, said cluster having first and second ends, the first end having a plurality of nodes each connecting to corresponding one of the first shell elements and the second end having a plurality of nodes each connecting to corresponding one of the second shell elements;

determining an average axial stress sensitivity scale factor and an average shear stress sensitivity scale factor for each end of the first and second ends;

determining an average location sensitivity scale factor of said each end of the first and second ends;

calculating force and moment resultants at said each end in current solution cycle;

calculating an overall plastic strain rate at said each end using plastic strain calculated in the current solution cycle and stored plastic strain in previous solution cycle of the time-marching simulation;

checking spot weld failure criterion at said each end, in which the calculated force and moment resultants, the plastic strain rate, and the average axial stress sensitivity scale factor, the average shear stress sensitivity scale factor and the average location sensitivity scale factor are used; and when the spot weld failure criterion indicates failure or rupture of the spot weld at either end of the first and second ends of the cluster, removing the cluster from the finite element analysis model for future solution cycles of the time-marching simulation.

12. The computer-readable storage medium of claim 11, the step of determining the average axial stress sensitivity scale factor and the average shear stress sensitivity scale factor for said each end, further comprises:

determining a plurality of individual axial stress sensitivity scale factors and a plurality of individual shear stress sensitivity scale factors of each of the nodes of said each end;

deriving the average axial stress sensitivity scale factor by averaging all of the individual axial stress sensitivity scale factors at said each end; and deriving the average shear stress sensitivity scale factor by averaging all of the individual shear stress sensitivity scale factors at said each end.

13. The computer-readable storage medium of claim 11, the step of determining the average location sensitivity scale factor of said each end, further comprises:

determining a plurality of individual location sensitivity scale factors of each of the nodes of said each end; and
deriving the average location sensitivity scale factor by averaging all of the individual location sensitivity scale factors at said each end.

14. The computer-readable storage medium of claim 11, the step of calculating the force and moment resultants further comprises:

when more than one solid elements are in the cluster,
grouping said more than one solid elements by a unique spot weld identification; and deriving the force and moment resultants by totaling individual force and moment of all of said more than one solid elements in the cluster.

15. The computer-readable storage medium of claim 11, the step of calculating the overall plastic strain rate at said each end further comprises:
    calculating a plurality of individual plastic strain rates of each of the nodes of said each end; and
    deriving the overall plastic strain rate by averaging all of the individual plastic strain rates at said each end.

16. A system for determining spot weld failure in a time-marching simulation of a structure impact event for designing a structure with one or more spot welds contained therein, the system comprising:
    a main memory for storing computer readable code for an application module;
    at least one processor coupled to the main memory, said at least one processor executing the computer readable code in the main memory to cause the application module to perform operations by a method of:
    receiving one or more spot weld definitions in a structure, each of the spot weld definitions includes a spot weld along with first and second parts connected therewith;
    creating a finite element analysis model of the structure including a cluster of at least one solid element to represent the spot weld, a plurality of first shell elements to represent the first part, and a plurality of second shell elements to represent the second part, said cluster having first and second ends, the first end having a plurality of nodes each connecting to corresponding one of the first shell elements and the second end having a plurality of nodes each connecting to corresponding one of the second shell elements;
    determining an average axial stress sensitivity scale factor and an average shear stress sensitivity scale factor for each end of the first and second ends;
    determining an average location sensitivity scale factor of said each end of the first and second ends;
    calculating force and moment resultants at said each end in current solution cycle;
    calculating an overall plastic strain rate at said each end using plastic strain calculated in the current solution cycle and stored plastic strain in previous solution cycle of the time-marching simulation;
    checking spot weld failure criterion at said each end, in which the calculated force and moment resultants, the plastic strain rate, and the average axial stress sensitivity scale factor, the average shear stress sensitivity scale factor and the average location sensitivity scale factor are used; and
    when the spot weld failure criterion indicates failure or rupture of the spot weld at either end of the first and second ends of the cluster, removing the cluster from the finite element analysis model for future solution cycles of the time-marching simulation.

17. The system of claim 16, the operation of determining the average axial stress sensitivity scale factor and the average shear stress sensitivity scale factor for said each end, further comprises:
    determining a plurality of individual axial stress sensitivity scale factors and a plurality of individual shear stress sensitivity scale factors of each of the nodes of said each end;
    deriving the average axial stress sensitivity scale factor by averaging all of the individual axial stress sensitivity scale factors at said each end; and
    deriving the average shear stress sensitivity scale factor by averaging all of the individual shear stress sensitivity scale factors at said each end.

18. The system of claim 16, the operation of determining the average location sensitivity scale factor of said each end, further comprises:
    determining a plurality of individual location sensitivity scale factors of each of the nodes of said each end; and
    deriving the average location sensitivity scale factor by averaging all of the individual location sensitivity scale factors at said each end.

19. The system of claim 16, the operation of calculating the force and moment resultants further comprises:
    when more than one solid elements in the cluster,
    grouping said more than one solid elements by a unique spot weld identification; and
    deriving the force and moment resultants by totaling individual force and moment of all of said more than one solid elements in the cluster.

20. The system of claim 16, the operation of calculating the overall plastic strain rate at said each end further comprises:
    calculating a plurality of individual plastic strain rates of each of the nodes of said each end; and
    deriving the overall plastic strain rate by averaging all of the individual plastic strain rates at said each end.

* * * * *